United States Patent
Wang et al.

(10) Patent No.: US 8,696,579 B2
(45) Date of Patent: Apr. 15, 2014

(54) CARDIAC FLOW QUANTIFICATION WITH VOLUMETRIC IMAGING DATA

(75) Inventors: Yang Wang, Plainsboro, NJ (US); Bogdan Georgescu, Plainsboro, NJ (US); Saurabh Datta, Cupertino, CA (US); Dorin Comaniciu, Princeton Junction, NJ (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 130 days.

(21) Appl. No.: 13/151,803

(22) Filed: Jun. 2, 2011

(65) Prior Publication Data

US 2011/0301466 A1 Dec. 8, 2011

Related U.S. Application Data

(60) Provisional application No. 61/351,340, filed on Jun. 4, 2010, provisional application No. 61/407,960, filed on Oct. 29, 2010.

(51) Int. Cl.
*A61B 8/00* (2006.01)

(52) U.S. Cl.
USPC ........... 600/454; 600/407; 600/437; 600/438; 600/450; 382/128; 382/130; 382/131

(58) Field of Classification Search
USPC ................. 600/407, 437, 438, 440, 450, 454; 382/128, 131
See application file for complete search history.

(56) References Cited

U.S. PATENT DOCUMENTS

| | | | |
|---|---|---|---|
| 5,724,974 A | 3/1998 | Goodsell, Jr. et al. | |
| 6,110,118 A | 8/2000 | Guracar et al. | |
| 6,527,717 B1 | 3/2003 | Jackson et al. | |
| 7,153,268 B2 | 12/2006 | Li et al. | |
| 7,288,068 B2 | 10/2007 | Bakrioglu et al. | |
| 7,828,735 B2 * | 11/2010 | Holmes et al. | 600/450 |
| 7,916,919 B2 | 3/2011 | Zheng et al. | |
| 8,280,136 B2 * | 10/2012 | Gotardo et al. | 382/131 |
| 2004/0254465 A1 | 12/2004 | Sano et al. | |
| 2005/0049500 A1 * | 3/2005 | Babu et al. | 600/443 |
| 2006/0058675 A1 * | 3/2006 | Olstad | 600/450 |
| 2006/0064017 A1 * | 3/2006 | Krishnan et al. | 600/450 |
| 2006/0171586 A1 * | 8/2006 | Georgescu et al. | 382/173 |
| 2007/0016037 A1 * | 1/2007 | Houle et al. | 600/438 |

(Continued)

FOREIGN PATENT DOCUMENTS

WO 99/55233 A1 11/1999

OTHER PUBLICATIONS

European Search Report dated Oct. 19, 2011.

(Continued)

*Primary Examiner* — Baisakhi Roy
(74) *Attorney, Agent, or Firm* — Michele L. Conover

(57) ABSTRACT

A method quantifies cardiac volume flow for an imaging sequence. The method includes receiving data representing three-dimensions and color Doppler flow data over a plurality of frames, constructing a ventricular model based on the data representing three-dimensions for the plurality of frames, the ventricular model including a sampling plane configured to measure the cardiac volume flow, computing volume flow samples based on the sampling plane and the color Doppler flow data, and correcting the volume flow samples for aliasing based on volumetric change in the ventricular model between successive frames of the plurality of frames.

20 Claims, 12 Drawing Sheets

(56) References Cited

U.S. PATENT DOCUMENTS

| | | | |
|---|---|---|---|
| 2007/0167794 | A1 | 7/2007 | Dala-Krishna |
| 2007/0255136 | A1 | 11/2007 | Kristofferson et al. |
| 2008/0051661 | A1 | 2/2008 | Kataguchi et al. |
| 2009/0226058 | A1* | 9/2009 | Li et al. ............... 382/128 |
| 2009/0306503 | A1 | 12/2009 | Srinivasan |
| 2010/0249589 | A1* | 9/2010 | Lysyansky et al. ........ 600/440 |
| 2012/0157851 | A1* | 6/2012 | Zwirn ...................... 600/447 |

OTHER PUBLICATIONS

Wang, et al.: "Learning-Based 3D Myocardial Motion Flow Estimation Using High Frame Rate Volumetric Ultrasound Data," In: ISBI, p. 1097-1100 (2010).

Matsumura, et al.: "Geometry of the Proximal Isovelocity Surface Area in Mitral Regurgitation by 3-Dimensional Color Doppler Echocardiography: Difference Between Functional Mitral Regurgitation and Prolapsed Regurgitation," American Heart Journal 155(2), p. 231-238 (2008).

Tenenbaum, et al.: "A Global Geometric Framework for Nonlinear Dimensionality Reduction," Science 290(5500), p. 2319-2323 (2000).

Zheng, et al.: "Four-Chamber Heart Modeling and Automatic Segmentation for 3-D Cardiac CT Volumes Using Marginal Space Learning and Steerable Features," TMI 27(11) p. 1668-1681, (2002).

Zoghbi, et al.: Recommendations for Evaluation of the Severity of Native Valvular Regurgitation with Two Dimensional and Doppler Echocardiography, Journal of the American Society of Echocardiography, 16(7) p. 777-802 (2003).

Little, S.H.: "Quantifying Mitral Valve Regurgitation: New Solutions From the 3rd Dimension," Journal of the American Society of Echocardiography 23(1), p. 9-12 (2010).

Yosefy, et al., "Proximal Flow Convergence Region as Assessed by Real-Time 3-Dimensional Echocardiography: Challenging the Hemispheric Assumption," Journal of the American Society of Echocardiography, vol. 20, No. 4, p. 389-396, Apr. 2007.

Plicht, et al., "Direct Quantification of Mitral Regurgitant Flow Volume by Real-Time Three-Dimensional Echocardiography Using Dealiasing of Color Doppler Flow at the Vena Contracta," Journal of the American Society of Echocardiography, vol. 21, No. 12, p. 1337-1346, Dec. 2006.

Zhu, et al., "A Dynamical Shape Prior for LV Segmentation from RT3D Echocardiography," MICCAI 2009, Part I, LNCS 5761, p. 206-213 (2009).

Skaug, et al., "Quantification of Mitral Regurgitation Using High Pulse Repetition Frequency Three-Dimensional Color Doppler," Journal of the American Society of Echocardiography, vol. 23, No. 1, p. 1-8, Jan. 2010.

Tu, "Probabilistic Boosting-Tree: Learning Discriminative Models for Classification, Recognition, and Clustering", ICCV, pp. 1589-1596 (2005).

* cited by examiner

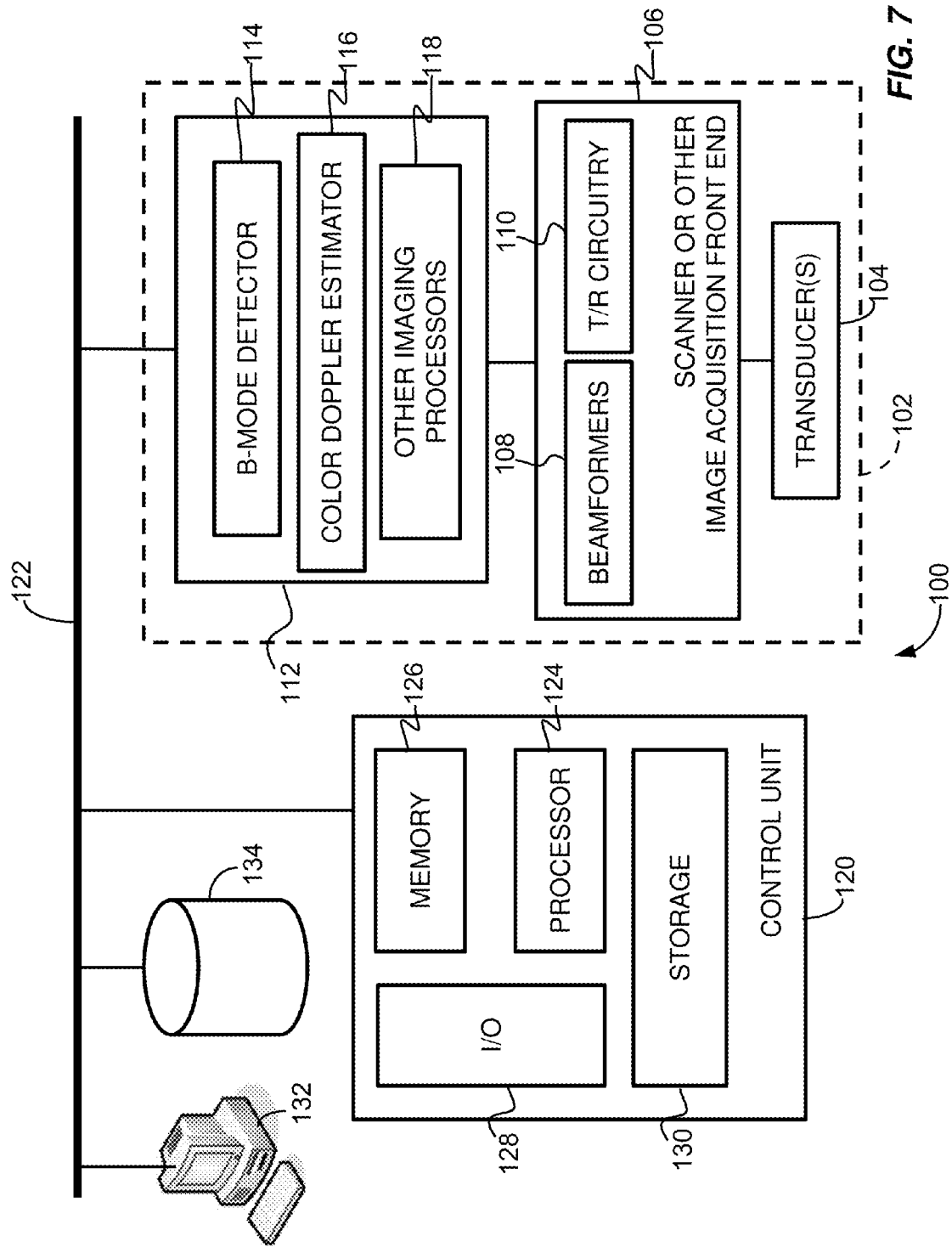

FLOW

FRAME

CARDIAC FLOW QUANTIFICATION WITH VOLUMETRIC IMAGING DATA

CROSS-REFERENCES TO RELATED APPLICATIONS

This application claims the benefit of U.S. provisional applications entitled "Automatic 3D Mitral and LVOT Flow Quantification on Volumetric Ultrasound Data," filed Jun. 4, 2010, and assigned Ser. No. 61/351,340, and entitled "Automatic Cardiac Flow Quantification on 3D Volume Color Doppler Data," filed Oct. 29, 2010, and assigned Ser. No. 61/407,960, the entire disclosures of which are hereby incorporated by reference.

BACKGROUND

The present embodiments relate to quantification of cardiac flow based on three-dimensional (3D) or volumetric imaging.

Valvular heart diseases are recognized as a significant cause of morbidity and mortality. Accurate quantification of cardiac volume flow in patients aids in the evaluation of the progression of the disease and in the determination of clinical options. The quantification of the volume of flow may assist in the evaluation of patients with other cardiac dysfunction and cardiovascular disease.

Recent advances in real-time, 3D full volume echocardiography have enabled high frame rate acquisition of volumetric color flow images. However, accurate flow quantification remains a significant challenge for cardiologists.

Doppler ultrasound is a non-invasive and cost-effective method for evaluation of intracardiac blood flow, for assessment of cardiac function, for estimation of shunt flows in congenital cardiac defects, and for assessment of regurgitation in the presence of valvular disease. With real-time, full volume echocardiography, it is now feasible to acquire transthoracic 3D color flow images (CFI) for every heartbeat (without stitching) such that both mitral valve and LVOT flow can be covered individually or together by the color Doppler region of interest.

However, a fundamental limitation of color Doppler data, flow velocity aliasing, remains a problem. Aliasing can introduce significant errors in flow quantification directly using color Doppler data. Attempts to overcome the velocity ambiguity have relied on customized hardware or geometric assumptions based on the recognition that ultrasound data alone is insufficient when true velocity is several multiples of the Nyquist level.

SUMMARY

By way of introduction, the embodiments described below include methods, systems, and apparatuses for cardiac flow quantification from data for three-dimensional imaging. The cardiac flow is quantified through construction of a ventricular model for an imaging sequence having a plurality of frames. The ventricular model is representative of the data in both a spatial and temporal manner. The ventricular model includes one or more sampling planes configured to collect flow samples from the imaging data. The ventricular model may be used to improve flow quantification, including, for instance, as a correction for aliasing.

In a first aspect, a method of quantifying cardiac volume flow for an imaging sequence includes receiving data representing three-dimensions and color Doppler flow data over a plurality of frames, constructing a ventricular model based on the data representing three-dimensions for the plurality of frames, the ventricular model including a sampling plane configured to measure the cardiac volume flow, computing volume flow samples based on the sampling plane and the color Doppler flow data, and correcting the volume flow samples for aliasing based on volumetric change in the ventricular model between successive frames of the plurality of frames.

In a second aspect, a system for quantifying cardiac volume flow for an imaging sequence includes an image acquisition system configured to capture data representing three dimensions and color Doppler flow data over a plurality of frames, and a processor in communication with the image acquisition system to receive the data representing three dimensions and the color Doppler flow data. The processor is configured to construct a ventricular model based on the data representing three dimensions, the ventricular model being configured to track motion of a ventricular boundary between successive frames of the plurality of frames, define a sampling plane based on the ventricular model for a first frame of the plurality of frames, the sampling plane being configured to measure the cardiac volume flow, adjust the sampling plane for a second frame of the plurality of frames based on the motion tracked by the ventricular model, and sample the color Doppler flow data for the second frame via the adjusted sampling plane.

In a third aspect, an ultrasound apparatus for quantifying cardiac volume flow for an imaging sequence includes an ultrasound beamformer configured to generate respective scan signals for a plurality of frames, a B-mode detector in communication with the ultrasound beamformer and configured to generate three-dimensional (3D) ultrasound image data from the scan signals, a flow estimator in communication with the ultrasound beamformer and configured to generate flow data from the scan signals, and a processor in communication with the B-mode detector and the flow estimator to receive the 3D ultrasound image data and the flow data. The processor is configured to construct a ventricular model based on the 3D ultrasound image data, the ventricular model being configured to track motion of a ventricular boundary between successive frames of the plurality of frames, define a sampling plane based on the ventricular model for a first frame of the plurality of frames, the sampling plane being configured to measure the cardiac volume flow, adjust the sampling plane for a second frame of the plurality of frames based on the motion tracked by the ventricular model, compute the cardiac volume flow for the second frame based on the adjusted sampling plane and the color Doppler flow data, and correct the computed cardiac volume flow for aliasing based on volumetric change in the ventricular model between the first and second frames of the plurality of frames.

The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

FIG. 7 is a block diagram of an example embodiment of an ultrasound system and apparatus for implementing the flow volume quantification methods and procedures described herein.

DETAILED DESCRIPTION OF THE PRESENTLY PREFERRED EMBODIMENTS

Figure 1:
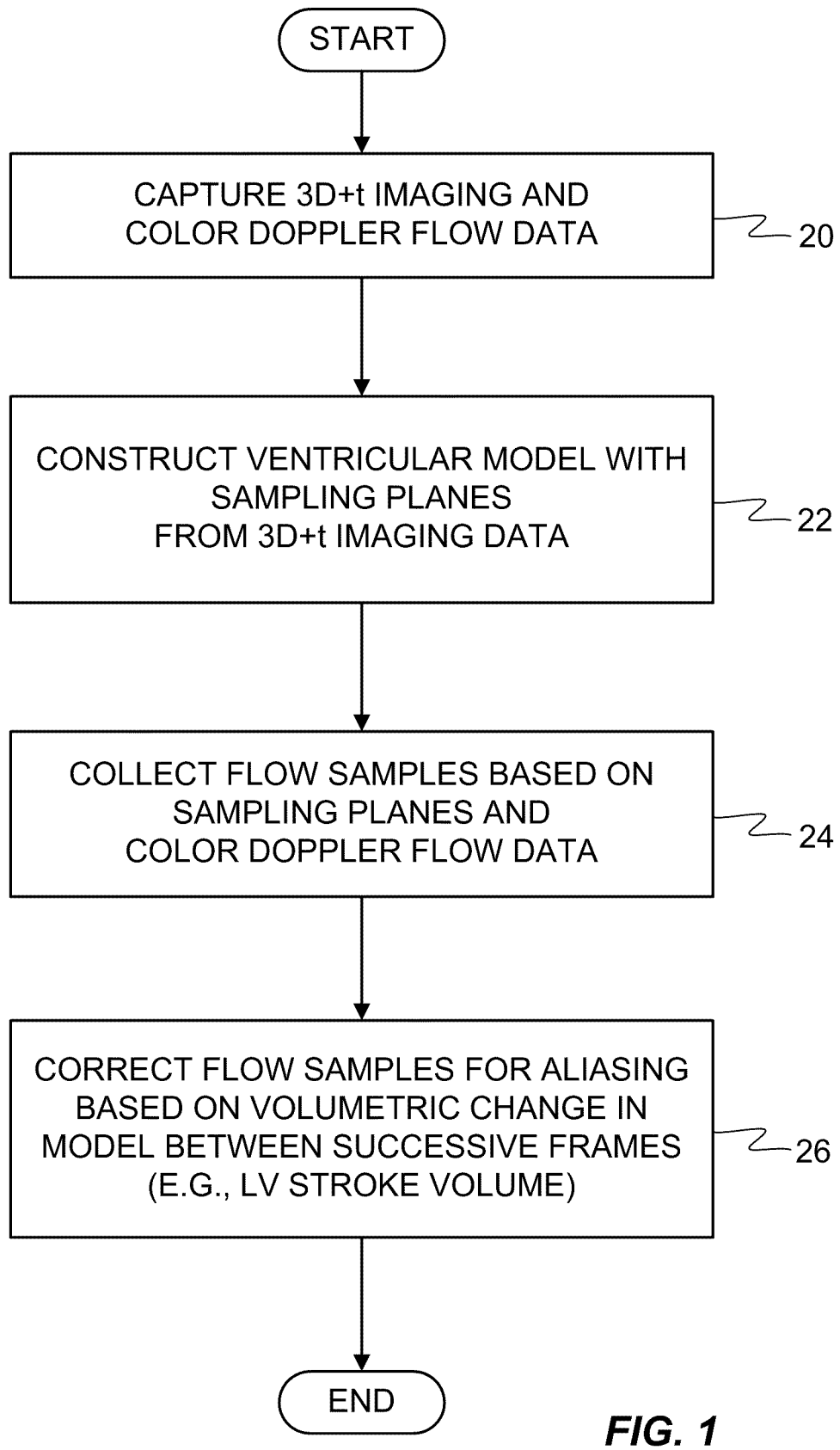
FIG. 1 is a flow chart diagram of an example embodiment of a method for quantifying cardiac flows from volumetric and color Doppler flow data.

Cardiac flow using imaging data, such as 3D+t (time) (4D) ultrasound and color Doppler data, may be used for quantification. Cardiac volume flow may be estimated in a fully automatic process. Anatomical information, such as mitral annulus and left ventricle outflow tract (LVOT), may be detected and tracked automatically to account for heart motion during an imaging sequence, which may include one or more heart beats. Anatomical boundaries, such as the endocardial boundary of the left ventricle (LV), are automatically detected and/or tracked. The detected and tracked boundaries support the computation of the instantaneous change in LV volume (i.e., LV stroke volume). This information may be used to overcome velocity ambiguity, such that de-aliasing parameters may be computed and used to correct flow computations. The relationship between flow volume and LV stroke volume is used to improve the flow quantification. Cardiac volume flows quantified using this process may agree with clinical data, and the quantification techniques described herein may be efficient, achieving high speed performance (e.g., 0.2 seconds per frame of data representing a volume).

The cardiac volume flow quantification techniques described herein use may use 3D+t ultrasound data (i.e., volumetric ultrasound over time) to construct a ventricular model. The 3D+t data is used to automatically detect both the mitral annulus and LVOT and place sampling or measurement planes at appropriate locations. The construction of these aspects of the ventricular model may be learning-based. To compensate for non-rigid heart motion, the sampling or measurement planes are tracked through the imaging sequence, e.g., one entire cardiac cycle or multiple cardiac cycles, to adjust and optimize the sampling locations and orientations in each frame. As a result, the flow volumes are computed consistently based on the anatomical structure of the left ventricle (LV).

A de-aliasing factor is generated for the color Doppler flow data. In this aspect, the LV volume change is estimated by automatically detecting and tracking the endocardial boundary. The de-aliasing factor is then determined based on the LV volume change, and used to correct the volume of the cardiac flow, e.g., mitral inflow or LVOT outflow. Alternatively or additionally, a de-aliasing factor is generated using the volume color Doppler flow data inside the left ventricle (LV). The net change in the spatial volume of the color Doppler data is used to estimate a de-aliasing factor to correct the volume of the cardiac flow, e.g. mitral inflow or LVOT outflow. This factor may be used in addition to or instead of the LV volume information in correcting for aliasing.

Although described below in connection with ultrasound apparatus and imaging data, the disclosed methods and systems are not limited to use with ultrasound imaging. Other imaging modalities capable of three-dimensional, high-resolution imaging may be used, including, for instance, magnetic resonance (MR) imaging and computed tomography (CT) imaging. These imaging modalities may be used to capture data representative of the ventricular boundaries, other anatomical structures, and/or other spatial information used to construct a ventricular model and sampling planes thereof. The disclosed methods provide a framework and technique that may be applied to other modalities and volumetric data that capture, for instance, 3D data capable of supporting non-rigid object deformation parameters and volume changes described below. For example, cardiac magnetic resonance (CMR) imaging may be used as an alternative modality for capturing 4D flow data. Information from multiple modalities may be combined to support the quantification methods.

FIG. 1 depicts a flow diagram of one embodiment for flow quantification. A learning-based technique estimates multiple cardiac flows, including, for instance, mitral inflow, LVOT outflow, and regurgitant flow. In act 20, data representing a volume is captured via, or received from, for instance, an ultrasound system. The data may be representative of tissue, such as B-mode or harmonic mode data, or of the blood within the tissue, such as volume color Doppler data. Another set of data may represent flow, such as velocity or energy of flow. One example estimation technique for flow data is Doppler flow, but correlation may be used. The tissue and flow data may represent a volume over time, such as acquired via real-time 3D full volume echocardiography. However, the data need not be processed in real-time. In other cases, the data is captured before implementation of the disclosed methods. The acts of the disclosed method may then be implemented off-line.

The data is captured over a sequence of time segmented into a number of frames. The sequence may include one or more heart beats, or one or more cardiac cycles. Each frame represents a scan of the volume sufficient to form the data of the frame, such as a frame of flow data formed by scanning each line multiple times or B-mode data formed by scanning each line in the volume once.

After the tissue and flow data has been captured, an anatomical model of the heart ventricle is constructed in act 22. As described below, automatic anatomy detection is implemented to construct a three-dimensional, ventricular model. With the first frame of data, the endocardial boundary of the left ventricle (LV), the mitral annulus, and the left ventricular outflow tract (LVOT) may be detected using a marginal space learning (MSL) framework, as described below. The ventricular model is then expanded to cover the entire sequence of imaging data via further machine-learning procedures that track the motion in successive frames. The 3D motion of the left ventricle, including the ventricular wall, the mitral annulus and the LVOT, are estimated by fusing information from multiple sources, including optical flow, boundary detection, and motion prior templates.

Three-dimensional flow sampling then occurs in act 24 once the ventricular model is constructed for the sequence. The ventricular model includes a definition of one or more sampling planes configured for measurement of respective cardiac flows. For example, a sampling plane may be defined to measure mitral inflow or LVOT outflow. The sampling plane may be configured as a cross-sectional area positioned and oriented relative to the remainder of the ventricular model to measure the flow through the area. As described below, the tracked locations of the mitral annulus and LVOT are used to adjust or optimize the sampling planes for each successive frame in the sequence. Once the sampling planes are defined for each frame and each flow, the flow data is then sampled and aggregated in the three-dimensional space.

In de-aliasing act 26, the volume flow samples are corrected for aliasing artifacts. The de-aliasing technique is based on the volumetric change in the ventricular model between successive frames. As described further below in connection with one example, the LV stroke volume may be determined by computing the change in volume of the ventricular model between successive frames. That is, based on the tracked LV endocardial boundaries, the LV volume change is computed between neighboring frames to estimate a de-aliasing factor of the measured color Doppler flow data. The de-aliasing factor may be specific to that frame, or be generated for the entire sequence. Using the de-aliasing factor, corrected flow volumes may be computed for both the mitral inflow and the LVOT outflow.

Figure 2:
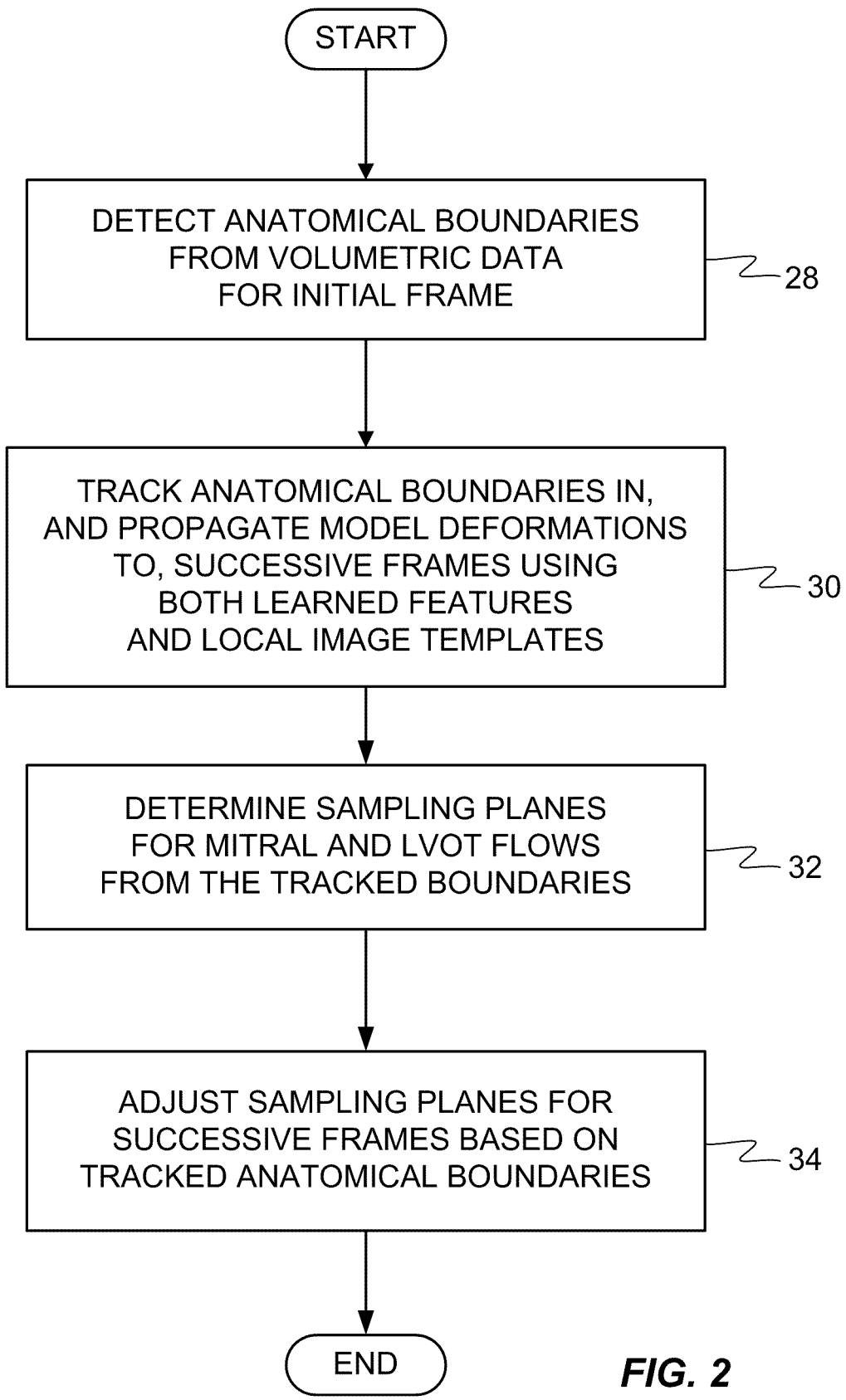
FIG. 2 is a flow chart diagram of a procedure for constructing and optimizing a volumetric and temporal ventricular model with sampling planes to support the quantization of the cardiac flows according to one embodiment.

FIG. 2 depicts further details regarding one example method for constructing the ventricular model. The ventricular model may be a 3D mesh model. In this example, the ventricular model is defined by, and includes, data representative of the anatomical structure of the left ventricle, mitral annulus, and LVOT. Additional, different or fewer anatomical structures may be used.

The construction of the ventricular model may begin in act 28. In act 28, the anatomical boundaries of the structures are detected in the imaging data for the initial or other frame of the sequence. The boundaries may be detected via one or more machine-learning techniques, such as the marginal space learning (MSL) framework described below. The ventricular model may also be based on one or more templates of the anatomical structures being modeled. The templates may provide a general model to be refined based on a machine learnt filter or model. For example, the ventricular model may include variances or deformations from template(s) trained using a machine and training data.

Alternatively or additionally to the above-described model construction technique, the construction of the model (and/or measurement of blood volume in the LV) may be performed by segmentation of color Doppler volume data in the LV. The change in the segmented color Doppler volume may provide an estimate of the temporal flow, which may be useful for determining a de-aliasing factor as described below.

The initial frame of the sequence may be defined or selected in a variety of automated techniques before the implementation of the model construction method. The initial frame defines the starting point for the flow quantification techniques described herein. The initial frame may thus be determined based on the flow volume(s) of interest. In one case, electrocardiograph (ECG) data may be analyzed to identify the time points for the initial and final frames, such as a beginning and end of a heart cycle. In cases where higher accuracy is desired, the ECG data may be optimized or adjusted via an analysis of the flow data. To that end, the flow data may be analyzed to determine when the mitral and LVOT flows begin and end. In one example, the initial frame corresponds with the end-diastole cardiac phase. In some cases, automatic adjustment of the beginning and ending time points is performed after the spatial ventricular model is constructed, including the detected mitral and LVOT sampling planes.

Once the ventricular model is constructed for the initial frame, the ventricular model may be extended to cover the remainder of the imaging sequence. In act 30, the anatomical boundaries are tracked to successive frames in the sequence. In this way, the ventricular model incorporates the motion of the anatomical structures during the imaging sequence. Tracking the boundaries may include the application of one or more machine-learnt classifiers. For example, the tracking may also utilize the learned features and local image templates involved in, or resulting from, the detection act 28. In this example, tracking the anatomical boundaries includes propagating any model deformations through the remainder of the imaging sequence.

The sampling planes for the cardiac flows are determined in act 32. In this example, respective sampling planes are defined for the mitral and LVOT flows. Each sampling plane is determined based on the anatomical boundaries of the ventricular model. Starting with the initial frame, the locations, orientations, and sizes of each sampling plane are determined from the ventricular model and, in some cases, the flow data. As described below, the sampling planes are then optimized or otherwise adjusted for the rest of the frames in the sequence. In this example, this optimization is shown as a separate act 34. Each optimization or adjustment accounts for the motion of the anatomical structures during the imaging sequence. Each sampling plane is thus defined on a frame-by-frame basis in accordance with the location and orientation of the anatomical boundaries of the model in each frame.

The order and implementation of the tracking and sampling plane determination acts may vary from the example shown. For example, the sampling planes for the initial frame may be determined before the boundaries are tracked throughout the imaging sequence, i.e., before the implementation of the tracking act 30. The sampling planes may be determined (e.g., adjusted) for a particular frame once the boundary tracking is completed for that frame. The remainder of the sampling plane determinations may then be implemented as the tracking act progresses through the imaging sequence. Once the model is extended to each successive frame in the sequence, the sampling planes for that frame may be defined. The sampling plane determinations may be integrated with the boundary tracking to any desired extent.

Figure 3:
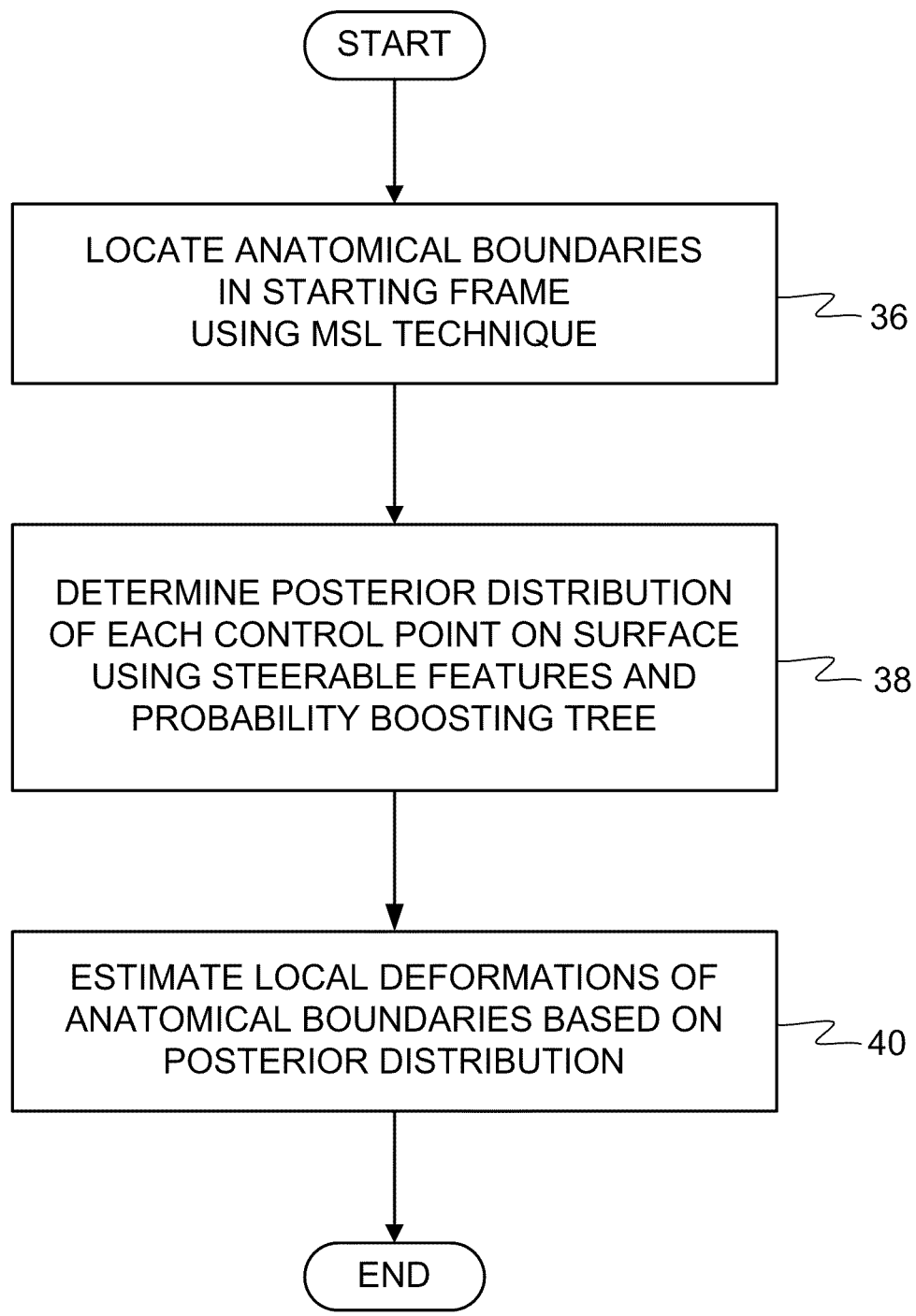
FIG. 3 is a flow chart diagram of a procedure for detecting anatomical boundaries to support the construction of the ventricular model according to one embodiment.

FIG. 3 describes one example of a learning-based anatomy detection technique that may be used to construct the ventricular model. In the initial or starting frame (e.g., the end-diastole cardiac phase), the endocardial boundary of the left ventricle (LV), the mitral annulus, and the LVOT are detected automatically based on the data. In act 36, the left ventricle is located using a machine trained detector. The machine trained detector may be trained using the marginal space learning (MSL) framework. For example, locating the left ventricle may include a determination of the pose of the anatomical boundaries, including the position X=(x, y, z), orientation θ=(α, β, γ), and scale S=($S_x$, $S_y$, $S_z$), of the left ventricle. The MSL framework provides a technique for detecting shapes and boundaries in high dimensional images. Implementation of the MSL framework reduces the number of testing hypotheses by incrementally learning classifiers on projected sample distributions, thereby avoiding an exhaustive search in the high dimensional parameter space. Instead, the space becomes more restricted by marginal space classifiers. Further details regarding marginal space learning are set forth in U.S. Pat. No. 7,916,919 ("System and method for segmenting chambers of a heart in a three dimensional image"), the entire disclosure of which is hereby incorporated by reference. Any features may be used for training the detector, such as Haar features.

In act 38, the posterior distribution $p_i(X|I)$ of each control point on the surface of the shape is located by application of the MSL framework. The posterior distribution $p_i(X|I)$ may be learned using steerable image features, a probability boosting-tree (PBT), and/or one or more other machine-learning techniques. Steerable image features incorporate orientation and scale information into the distribution of sampling points to allow for the avoidance of time-consuming volume data rotation operations. Steerable features provide an alternative to global, Haar, or local features to steer a sampling pattern rather than align a volume to a hypothesized orientation. Once the features are obtained, the features are used to train simple classifiers, as well as a probabilistic boosting tree (PBT). In this way, the simple classifiers are combined to get a strong classifier for the parameters of interest. Further details regarding the use of steerable feature techniques to detect LV and other anatomical boundaries and shapes are set forth in the above-referenced U.S. patent.

The ventricular model may include data representative of local deformations of the mitral annulus, LVOT, and myocardial boundaries. These deformations may be estimated in act 40 based on the posterior distribution $p_i(X|I)$ of each control point on the surface of the ventricular model. Further details regarding these machine learning frameworks and techniques are set forth in Z. Tu, "Probabilistic boosting-tree: Learning discriminative models for classification, recognition, and clustering," ICCV, p. 1589-1596 (2005). The data is applied to the machine learnt classifier. The output is locations with the greatest probability of being the boundaries.

Figure 4:
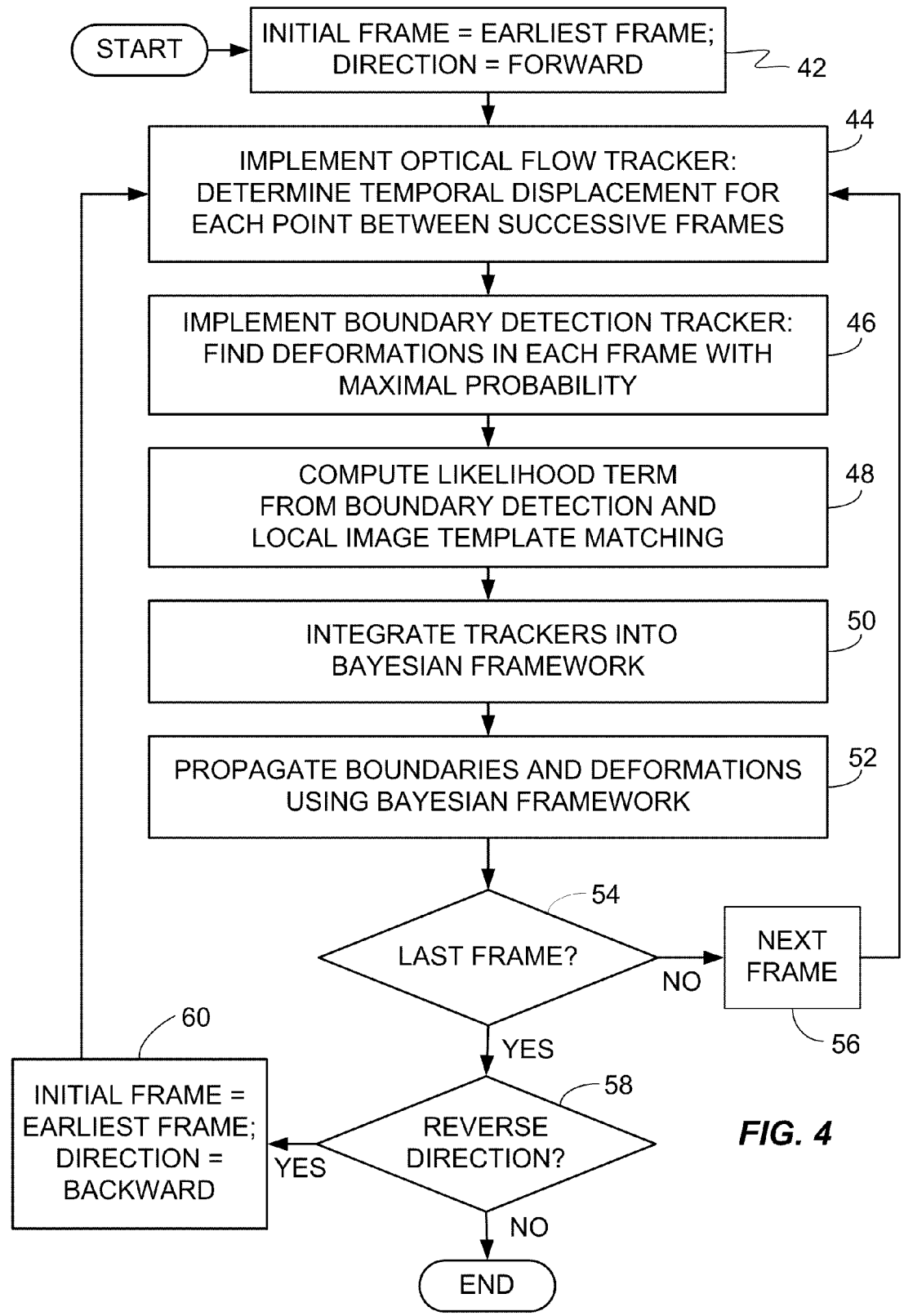
FIG. 4 is a flow chart diagram of a procedure for tracking motion of the anatomical boundaries to support the construction of the ventricular model according to one embodiment.

FIG. 4 depicts an example of a cardiac anatomy tracking method that extends the ventricular model to cover the remaining frames of the sequence. Starting from the detection result at the initial frame in act 42, the model deformations are propagated to neighboring frames using both the learned features and local image templates for the left ventricle. The local image templates may include data generally representative of the shape, pose, and other surface characteristics of the left ventricle to be optimized by the imaging data for construction of the ventricular model. To ensure temporal consistency and smooth motion and to avoid drifting and outliers, two collaborative trackers, an optical flow tracker and a boundary detection tracker, are used. The two trackers are implemented in acts 44 and 46, respectively. In this example, the optical flow tracker directly computes the temporal displacement for each point on the surface of the model from one frame to the next, while the detection tracker obtains the deformations in each frame with maximal probability. As described below, the boundary detection tracker uses the MSL framework to generate a set of classifiers indicative of the anatomical structures and their boundaries.

The boundary detection tracker is used in act 48 in conjunction with local image template matching to determine the likelihood term of a Bayesian framework. In this example, the likelihood term $p(\vec{Y}_t|\vec{X}_t)$ is computed from both boundary detection and local image template matching, as in $p(\vec{Y}_t|\vec{X}_t)=(1-\lambda)p(F_t|\vec{X}_t)+\lambda p(T_t|\vec{X}_t)$, where $F_t$ is the steerable feature response, $T_t$ is the local image template, and $\lambda$ is the weighting coefficient of the matching term. Further details regarding the use of steerable feature responses as part of the above-referenced machine learning techniques are set forth in Y. Zheng, et al., "Four-chamber heart modeling and automatic segmentation for 3-D cardiac CT volumes using marginal space learning and steerable features," TMI, Vol. 27, No. 11, p. 1668-1681 (2008).

The above two trackers are integrated in act 50 into a single Bayesian framework, with the assumption that the input images I are mutually independent:

$$\operatorname*{argmax}_{\vec{X}_t} p(\vec{X}_t | \vec{Y}_{1:t}) = \operatorname*{argmax}_{\vec{X}_t} p(\vec{Y}_t | \vec{X}_t) p(\vec{X}_t | \vec{Y}_{1:t-1}),$$

where $\vec{Y}_{1:t}=\vec{Y}_1, \ldots, \vec{Y}_t$ are the measurements from the first t frames $I_{1:t}=(I_1, \ldots, I_t)$. For clarity, we use $\vec{X}_t$ to denote a concatenation of the mesh point positions, $\vec{X}_t=[X_1, \ldots, X_n]$, which are estimated at the current time instance t, and n is the total number of points in the model.

Given the resulting shapes $\vec{X}_{1:t-1}$ from the previous t−1 frames, the prediction term $p(\vec{X}_t|\vec{Y}_{1:t-1})$ may be simplified as $p(\vec{X}_t|\vec{X}_{1:t-1})$ which may be learned from the training data set as set forth in Y. Wang, et al., "Learning-based 3D myocardial motion flow estimation using high frame rate volumetric ultrasound data," ISBI, p. 1097-1100 (2010).

The anatomical boundaries of the ventricular model, including any deformations, are propagated or otherwise extended in act 52 to that frame. The data of the frame is applied to the Bayesian framework to update the ventricular model for that frame. The foregoing tracking and deformation propagation acts are repeated until the full 4D (temporal and spatial) model is estimated for the complete sequence. In this way the collaborative trackers complement each other, as the optical flow tracker provides temporally consistent results and its major issue of drifting is addressed by the boundary detection tracker. In this example, a decision block 54 determines whether the last frame in the sequence has been reached. If not, control passes to act 56 that advances the procedure to the next frame in the sequence and returns control to act 44 for implementation of the tracking and propagation acts for that frame.

In this example, the tracking is performed in both forward and backward directions to obtain a smooth motion field. Due to the periodic nature of the cardiac motion, the foregoing tracking and deformation acts are first implemented in the forward direction through the sequence, as specified in act 42.

Once the last frame in the sequence has been reached, control passes to a decision block 58, which determines whether the processing is proceeding in a forward time direction through the sequence. If yes, then control passes to act 60 that reverses the direction for the processing and sets the initial frame to the earliest frame in the sequence. Control passes back to act 44 and the tracking and propagation procedure is implemented again in the reverse direction. Once the beginning of the sequence is reached after iterating through the tracking and propagation acts for each frame, the decision block 58 is reached again, and the procedure terminates with a complete four-dimensional (3D plus time) model for the entire imaging sequence. The imaging sequence may include any number of cardiac cycles, or any portion of a cardiac cycle. Alternatively, the processing in the forward and backward directions occurs simultaneously rather than in two separate procedures, in which case the processing may end when a frame in the middle of the sequence is reached.

A Gaussian kernel may be applied to the neighboring frames for further smoothing of the motion field over the sequence:

$$X_t^{smooth} = \Sigma_{i=-k}^{k} G(i) X_{t+i},$$

where $G(i)$ is a normalized Gaussian kernel $N(0,\sigma)$. For example, $\sigma$ may equal 0.6, and k may equal 1.

Figure 5:
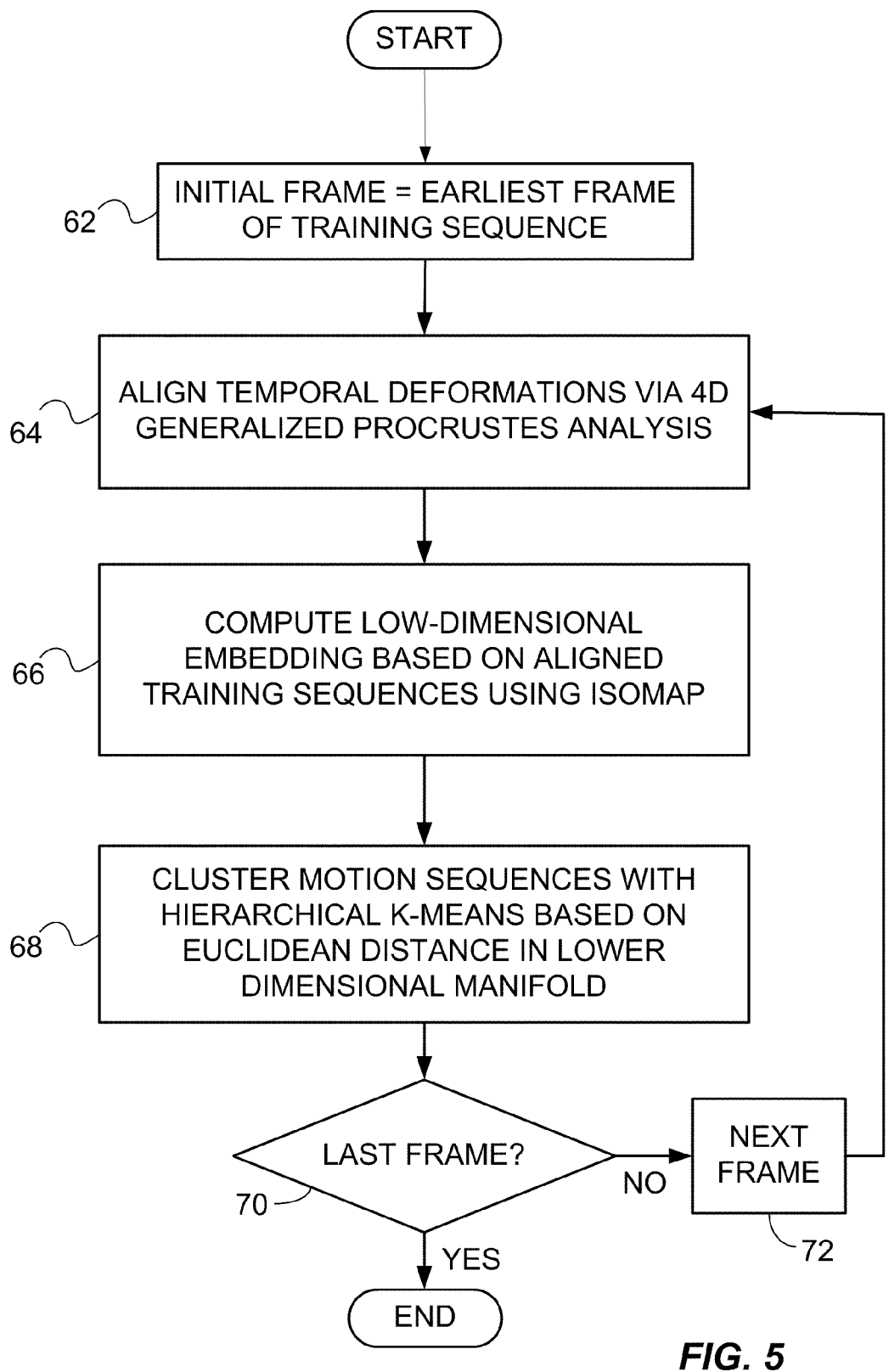
FIG. 5 is a flow chart diagram of a training stage procedure for estimating a prior probability distribution of motion (i.e., the "motion prior") to support the construction of the ventricular model according to one embodiment.

FIG. 5 depicts one example of a training stage procedure to support the foregoing 4D model construction method. The procedure provides an estimate for the motion prior probability distribution, or motion prior, term in the above-referenced Bayesian framework. The motion prior is estimated at a training stage from a pre-annotated database of sequences containing one cardiac cycle each. In this example, the estimation uses motion manifold learning and hierarchical K-means clustering.

Beginning with an initial frame in the training sequence established in act 62, temporal deformations are aligned by 4D generalized procrustes analysis in act 64. Next, a low-dimensional embedding is computed in act 66 from the aligned training sequences using the ISOMAP algorithm. In this way, the highly non-linear motion of the heart valves may be represented. Finally, in order to extract the modes of motion, the motion sequences are then grouped or classified in act 68 with hierarchical K-means clustering based on the Euclidean distance in the lower dimensional manifold. A decision block 70 determines whether the last frame in the training sequence is reached and, if not, passes control to act 72 that advances the procedure to the next frame. Once all of the frames in the training sequence have been processed, the motion of the anatomical structures is reduced to a lower dimension more easily processed in real-time to construct the 4D ventricular model on the current imaging data.

Further details on the ISOMAP algorithm are set forth in J. B. Tenenbaum, et al., "A global geometric framework for nonlinear dimensionality reduction," Science, Vol. 90, No. 5500, p. 2319-2323 (2000).

Figure 6:
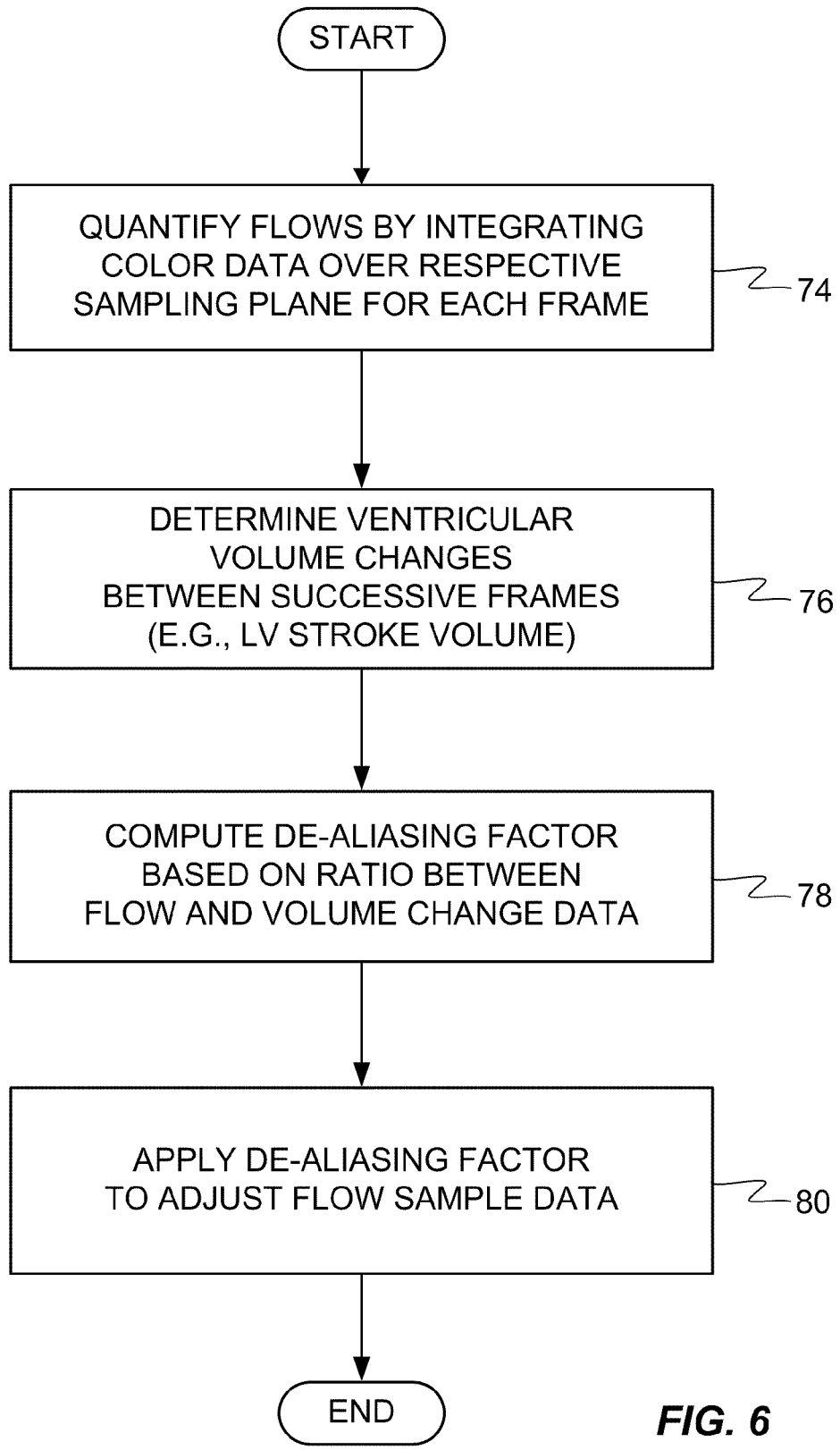
FIG. 6 is a flow chart diagram of a procedure for quantifying and correcting cardiac volume flow data via the sampling planes according to one embodiment.

FIG. 6 depicts further details regarding the flow computation and de-aliasing acts of the disclosed methods. Given the tracking result $\vec{X}$ for the anatomical model, one or more sampling planes are constructed to sample and compute the cardiac flow(s), e.g., the mitral and LVOT flows. Given a color flow image $F_t$ at the time instance t, the flow volume is computed in act 74 as an integral of the color measurements on the sampling plane:

$$VF_t^{ma} = dA \times VF_t^m / 128 / fr \times vs$$

$$VF_t^m = \Sigma_{i=1}^{N_S} F_t(\vec{X}(i))$$

where dA is the unit sampling area on the sampling plane, fr is the frame rate, vs is the velocity scale, $N_S$ is the number of non-zero samples on the sample plane, and $\vec{X}(i)$ is the 3D position of the i-th sampling area.

In flow data, aliasing is a common issue associated with single or multiple exceeding of the Nyquist velocity, which causes ambiguity for velocities beyond the Nyquist level. To address the aliasing issue, the LV volume $V_t$ may be computed based on the tracking result $\vec{X}$ for each frame t. As a result, the LV volume change may be computed in act 76 as the difference between two neighboring frames as follows:

$$dV_t = V_t - V_{t-1}$$

Because the LV volume change dV and the flow volume $VF_{ma}$ measure the same amount of blood flow through the left ventricle at a certain time instance, a de-aliasing factor of the color flow measurement may be computed in act 78 as the ratio between two volume values, i.e., $$f_{de} = \left\lfloor \frac{dV_t - VF_t^{ma}}{dA \times N_S / fr \times vs} \right\rfloor$$

where dA is the unit sampling area, $N_S$ is the number of nonzero samples on the sample plane, fr is the frame rate, and vs is the Doppler velocity scale, and $\lfloor x \rfloor$ is the floor function which returns the closest integer not greater than x. The de-aliasing factor may then be applied in act 80 to each flow value determined to correct for aliasing effects. The LV volume change reflects the global flow measurement, while the color Doppler data measures mitral and LVOT flow separately, which may aid the evaluation of valvular heart disease, such as mitral regurgitation. In case of regurgitation, the global change in LV volume will not be equal to the forward flow through the LVOT, as some flow will leak back into the atrium. If the LV data is not accurate or incomplete, the color Doppler provides an opportunity to compute more accurate flow.

In an alternative embodiment, the de-aliasing factor may be computed as the ratio between the two volume values, i.e., $$f_{de} = \frac{dV_t}{VF_t^{ma}}.$$

With reference to FIG. 7, the methods described above may be implemented by a system 100 that provides automatic detection and quantification of cardiac flow. The system 100 quantifies the flow volumes based on imaging data representative of anatomical and flow structures as described above, including, for instance, the endocardial boundary of the left ventricle, the mitral annulus, and the LVOT. The system 100 implements some or all of the above-described acts to provide flow tracking and 3D flow sampling based on detected boundary location(s) and simultaneous correction of flow. The correction may include de-aliasing based on the temporal change in LV cavity volume and the measured flow volume. The system 100 also optimizes the flow measurements both spatially and temporally by incorporating, for instance, the above-described cross-sectional profile adjustments based on both tissue (e.g., b-mode ultrasound) and flow data. The adjustment may use and fuse multiple sources of different types of information, including anatomic, electric (e.g., ECG), and functional information, as described above. Examples of functional information include the temporal change in LV cavity volume, which may be used to adjust the flow time points and to estimate the dealiasing factor, as well as the phase of the cardiac cycle, which may be used along with the corresponding expected flow direction.

The system 100 includes an image acquisition device or system 102. In the example shown in FIG. 7, the image acquisition device 102 is an ultrasound apparatus configured for real-time, 3D, full volume echocardiography. The ultrasound apparatus includes one or more transducers 104 directed by a scanner or front-end 106, which, in turn, includes a number of beamformers 108 and corresponding transmit/receive circuitry 110. The scanner 106 may include a number of additional components of a conventional ultrasound apparatus, including, for instance, an analog-to-digital converter and amplifiers in both the transmit and receive paths. The image acquisition device 102 also includes a data processing unit 112 that may include one or more processors for generating the imaging data from the data developed by the scanner 106. In this example, the data processing unit 112 includes a b-mode detector 114, a color Doppler estimator 116, and any number of other imaging processors 118, as desired.

The system 100 includes a control unit 120 configured to implement the above-described methods. The control unit 120 may include a personal computer, server computer, or any other computing device. The control unit 120 is in communication with the image acquisition device 102 to receive the imaging data developed by the data processing unit 112 upon completion of, or during, a scan sequence. In this example, the communication occurs via a network 122, the configuration of which may vary considerably. The control unit 120 includes a processor 124, a memory 126 (e.g., volatile and/or non-volatile) in communication with the processor 124, one or more input/output (I/O) interfaces 128 for further communication with the processor 124, and one or more data storage devices 130. In this example, the data storage device 130 stores information and data to support the construction of the ventricular model as described above. For example, the information may be representative of instructions configured to implement the above-described methods. The data may be representative of the captured imaging data, as well as any pre-existing data, such as training sequences and local image templates. Alternatively or additionally, the data storage devices 130 may include a scan library or other database to direct the image acquisition device 102 through a variety of scan sequences configured to capture ultrasound data to be processed by the flow volume quantification methods. The processor 124 and, more generally, the control unit 120 are configured to implement the above-described methods, procedures, and techniques for quantifying the cardiac volume flows. In alternative embodiments, the processor of the ultrasound system implements the above-described methods, procedures, and techniques.

The system 100 may include one or more operator consoles 132 in communication with the rest of the system 100 via the network 122. The operator console 132 may include a personal computer or other workstation configured to allow a user to control and otherwise interact with the other components of the system 100. The system 100 may also include any number of data stores 134 accessible to the other components of the system 100 via the network 134. The data store 134 may provide data storage for the captured imaging data or for the output of the control unit 120.

The above-described components of the system 100 need not communicate via a network, as the system 100 may alternatively or additionally include any number of direct communication links between the various components, devices, or subsystems. Other aspects of the system 100 may vary considerably, including the nature of the scanner or image acquisition front end 106 if, for instance, a different modality is used to capture the anatomical imaging data.

Figure 8A:
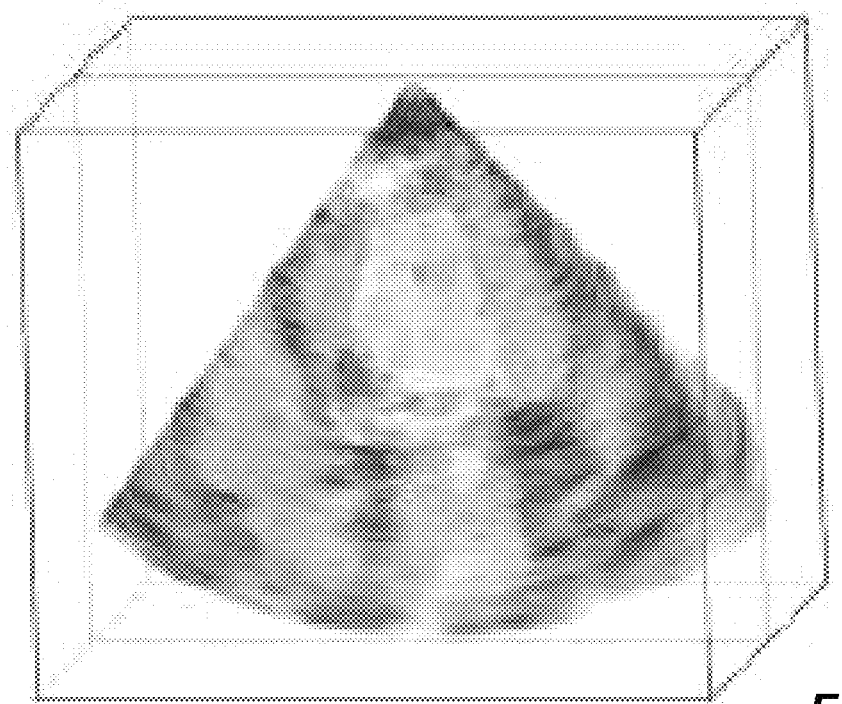
FIGS. 8A and 8B depict photographic representations of two example frames of volumetric ultrasound data, including color Doppler data, to support the construction of a ventricular model for use in the disclosed quantification methods.
Figure 8B:
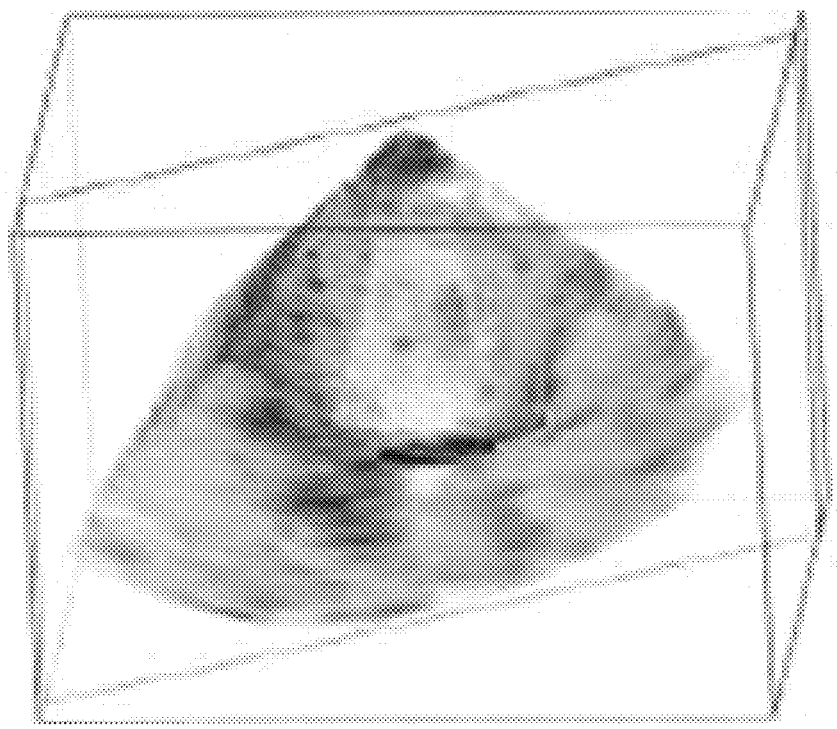

FIGS. 8A and 8B show examples of volumetric data that may be processed via the disclosed quantification methods. In FIG. 8A, a first frame of ultrasound imaging data is representative of the left ventricular wall, mitral annulus, and the LVOT at a first time instance during the imaging sequence. The same anatomical structures are represented by the ultrasound imaging data shown in FIG. 8B and captured at a second time instance during the imaging sequence. The above-described methods are configured to detect and track the anatomical structures through these and other frames of the imaging sequence to construct a ventricular model for the imaging data.

Figure 9A:
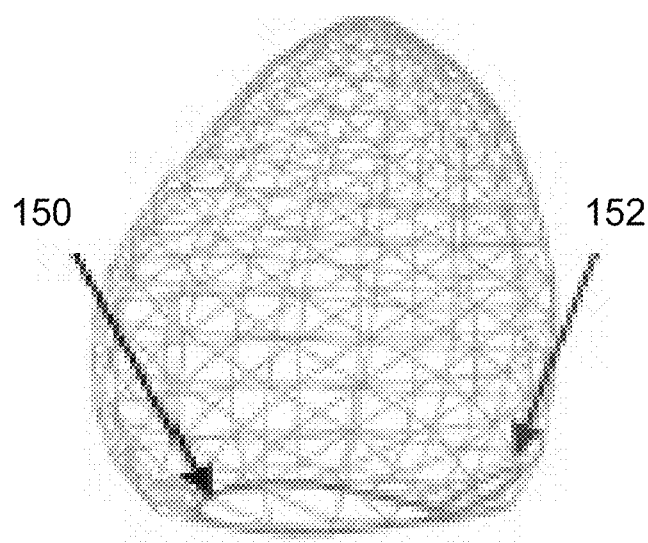
FIGS. 9A and 9B depict photographic representations of elevational and bottom views of a ventricular model, including sampling planes, constructed in accordance with one embodiment.
Figure 9B:
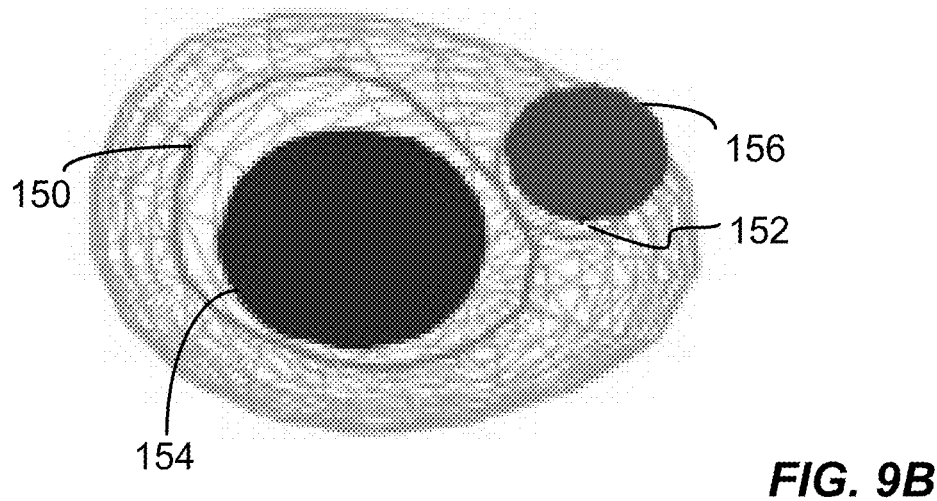

FIGS. 9A and 9B show one example of a ventricular model used to represent the left ventricle, mitral annulus, and left ventricular outflow tract (LVOT). In this example, the ventricular model is configured as a 3D mesh model. In FIG. 9A, the mitral annulus and the LVOT are represented by respective rings 150, 152. As shown in FIG. 9B, the ventricular model includes sampling planes 154, 156 for measuring the flow through the mitral annulus 150 and the LVOT 152, respectively. The LVOT sampling plane may be shifted in the drawing figures to a position away or spaced from the valve area to avoid flash noise.

Because of the physical form of the 3D ultrasound pyramid, a plane in the acoustic space with a constant distance to the transducer corresponds to a sphere in the Cartesian space, centering at the tip of the pyramid. Therefore, the sampling plane in the ventricular model is defined on a sphere passing through the mitral annulus 150 or the LVOT 152. To compute the integral volume of the mitral inflow and LVOT outflow, the flow data within the circular areas enclosed by the mitral annulus 150 and the LVOT ring 152 is integrated as described above.

Figure 10A:
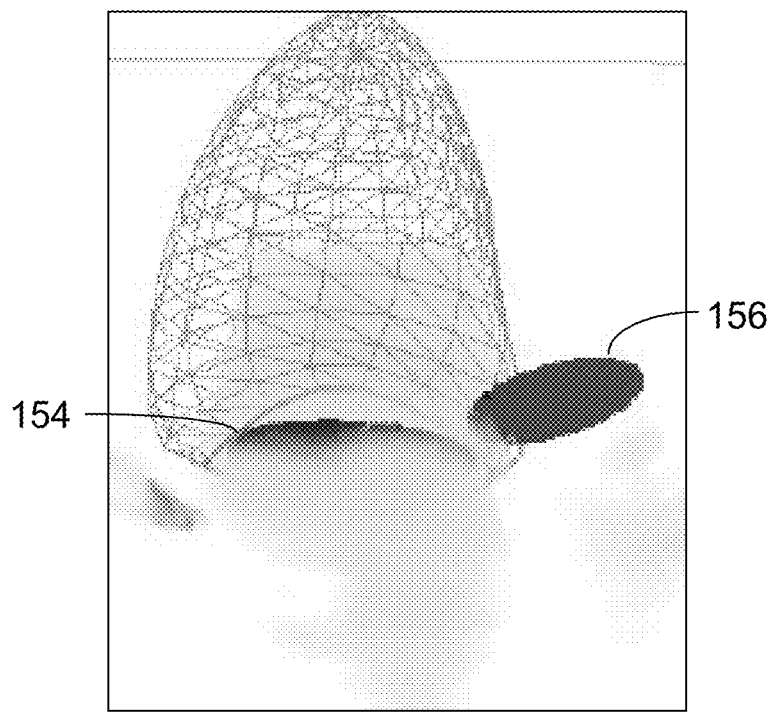
FIGS. 10A and 10B depict photographic representations of color Doppler flow data for respective frames of imaging data relative to the ventricular model of FIGS. 9A and 9B.
Figure 10B:
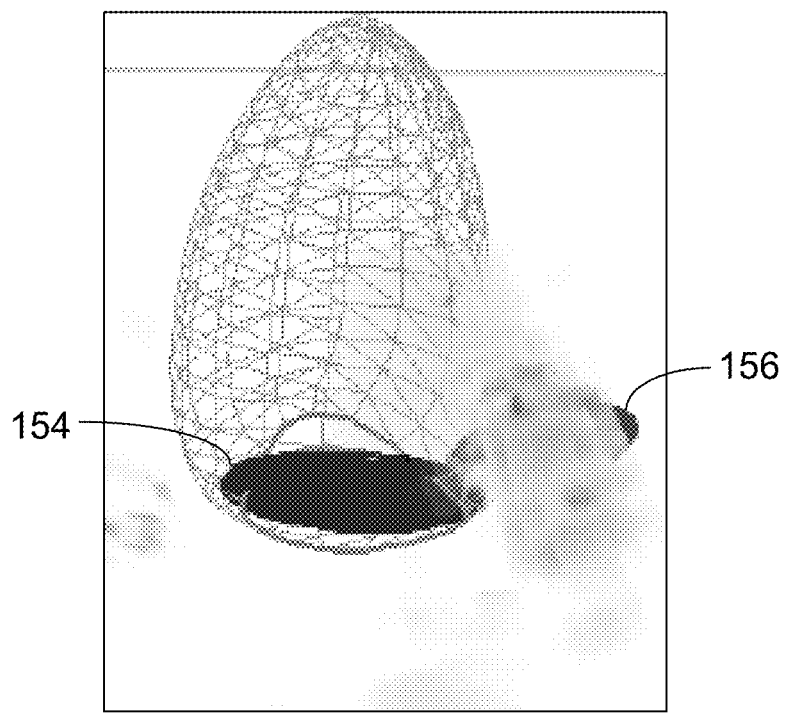

The ventricular model is also shown in FIGS. 10A and 10B with examples of color Doppler flow data relative to the sampling planes 154 and 156. FIGS. 10A and 10B show examples of flow sampling for two different frames in the imaging sequence. FIG. 10A shows mitral inflow, while FIG. 10B shows LVOT outflow.

To demonstrate performance, one example of the disclosed methods is evaluated on a clinical dataset taken from 22 subjects with normal valves via a Siemens SC2000 scanner with an average volume rate of 15 vps. The flow volume quantifications generated by the disclosed method are then compared with two routine clinical measurements, 2D quantitative Doppler with pulsed wave Doppler acquisition at LVOT to estimate LV stroke volume and LV stroke volume from 3D b-mode contouring of LV cavity. These measurement techniques are clinically accepted methods and independently validated elsewhere.

The comparison with the routine clinical measurements using 2D pulsed wave (PW) Doppler demonstrates the accuracy and robustness of the disclosed methods. The LV stroke volume (LVSV) is very close to the volume from LVOT-PW (70.1±20.8 ml, 69.7±16.7 ml) with good correlation (r=0.78). The 3-D LV inflow and outflow volumes quantified by the disclosed methods (73.6±16.3 ml, 67.6±14.6 ml) correlate well with LVSV and LVOT-PW, respectively (r=0.77; 0.91). Therefore, the quantified flow volumes are consistent and close to the routine clinical measurements.

Figure 11A:
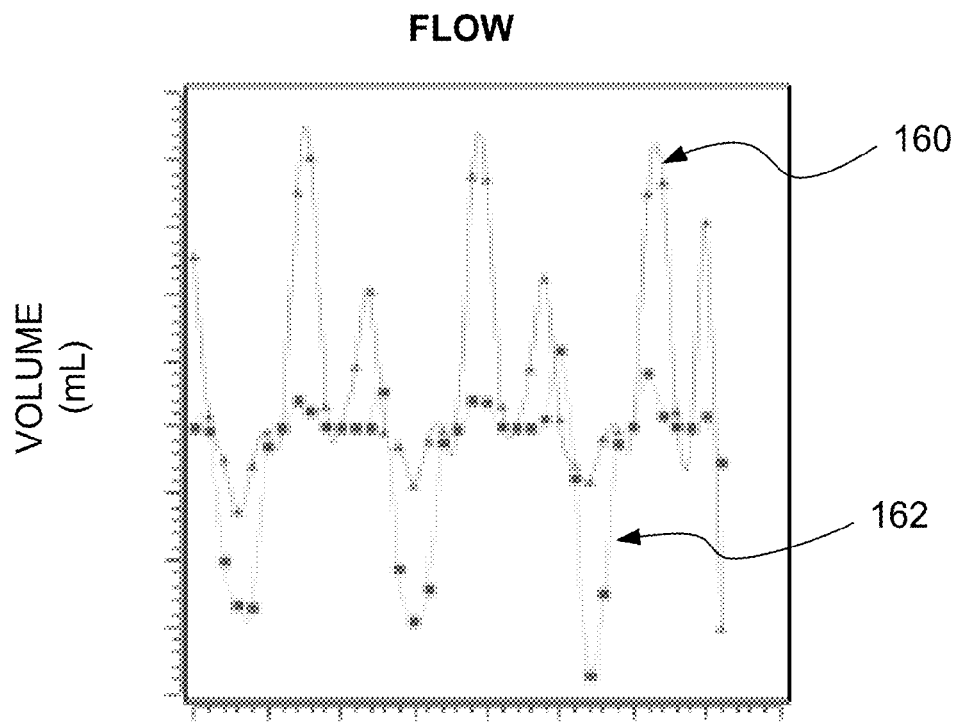
FIGS. 11A and 11B depict photographic representations of data plots of cardiac volume flow measurements from color flow images for a normal patient (i) with velocity aliasing, and (ii) after flow quantification (including de-aliasing) via a disclosed method, respectively.
Figure 11B:
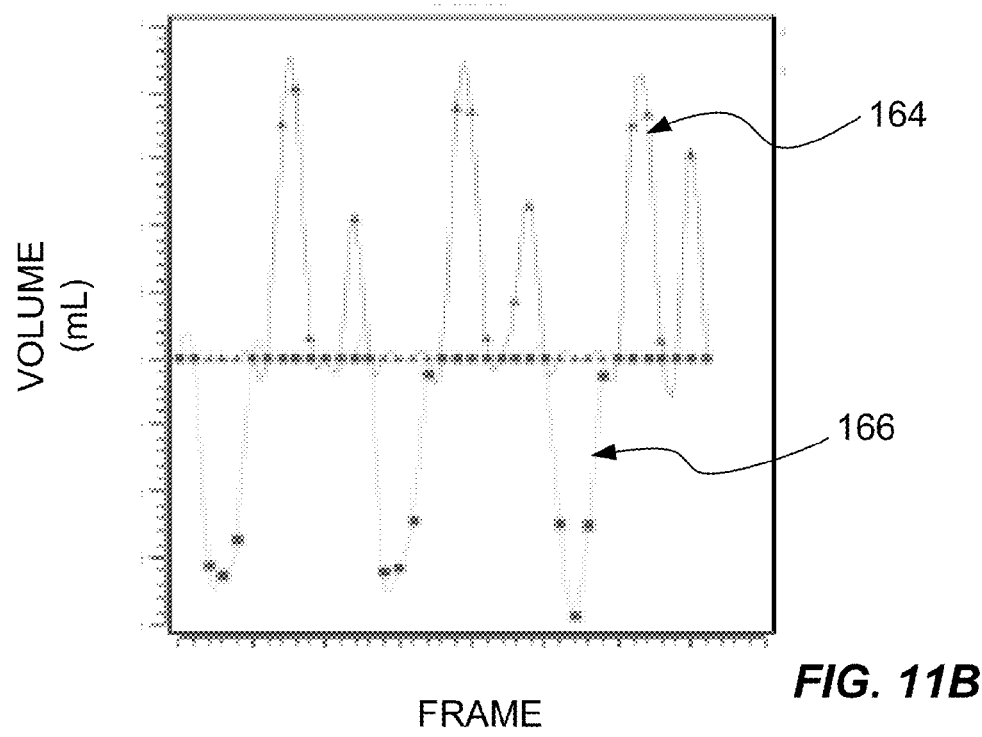

FIGS. 11A and 11B demonstrate the de-aliasing aspect of the disclosed methods in connection with a multi-beat sequence on a normal patient. FIG. 11A shows an aliased flow measurement sampled from the flow data, while FIG. 11B shows the resulting flow from our de-aliasing method. The input sequence has 37 volumes with 3 heart beats. Mitral inflow is plotted along curves 160 (FIG. 11A) and 164 (FIG. 11B), while LVOT outflow is plotted along curves 162 (FIG. 11A) and 166 (FIG. 11B). The de-aliased mitral inflow and LVOT outflow volume curves show a consistent pattern in all three cycles.

Figure 12A:
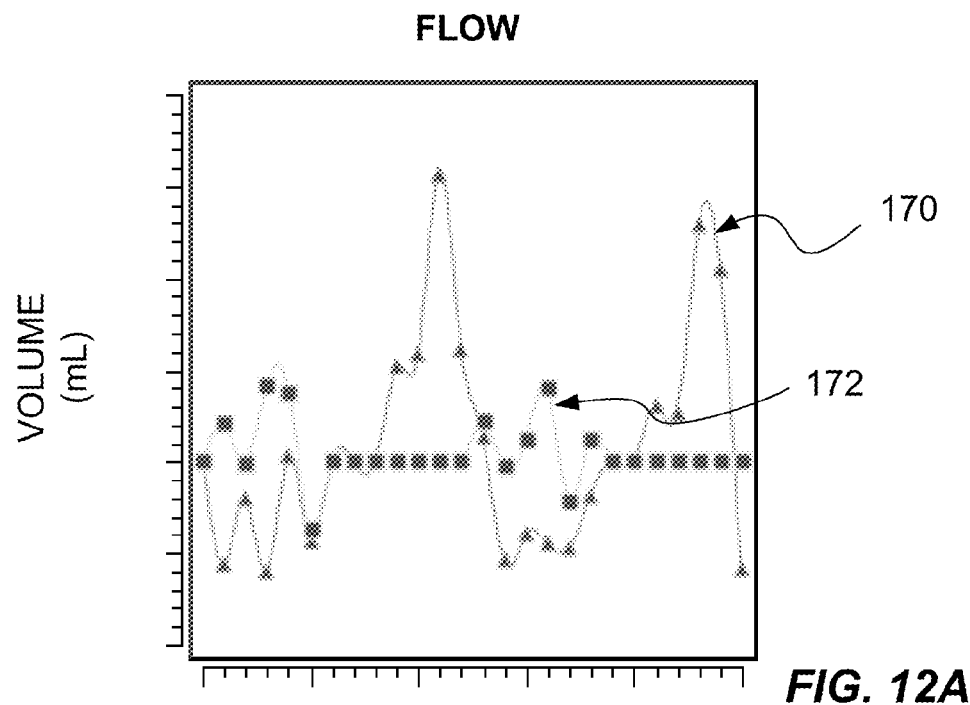
FIGS. 12A and 12B depict photographic representations of data plots of cardiac volume flow measurements from color flow images for a mitral regurgitation patient (i) with velocity aliasing, and (ii) after flow quantification (including de-aliasing) via a disclosed method, respectively.
Figure 12B:
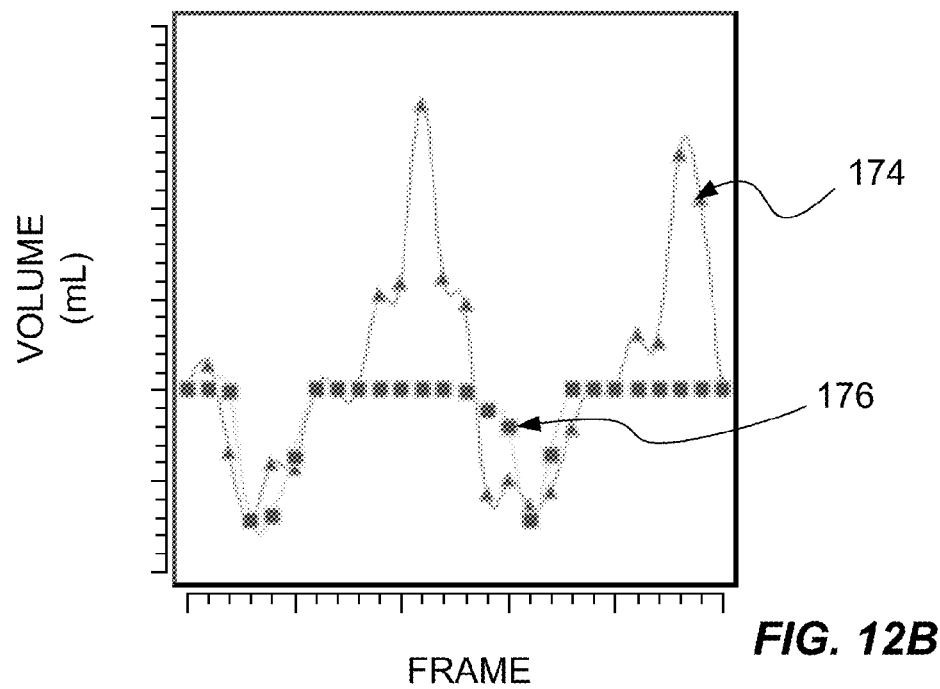

FIGS. 12A and 12B show the original (aliased) flow volume measurement from flow data with velocity aliasing, and the resulting flow volume corrected by the de-aliasing method, respectively. In this example, the 4D ultrasound sequences are acquired by a Siemens SC2000 scanner with an average volume size of size 200×200×140 and a resolution of 1 mm in the x, y and z directions. A multi-beat example is processed for a patient with mitral regurgitation. The input sequence has 26 frames with two heart beats. Mitral inflow is plotted along curves 170 (FIG. 12A) and 174 (FIG. 12B), while LVOT outflow is plotted along curves 172 (FIG. 12A) and 176 (FIG. 12B). The de-aliased flow volume values are consistent with the expert measurements in the clinical study in which the sequences were obtained.

Described above is a fully automatic method to estimate both mitral inflow and LVOT outflow on 3D real-time full volume ultrasound data. A 3D model is fitted automatically to the left ventricle (LV), mitral annulus, and LVOT to construct measurement planes in a volumetric color Doppler image. To compensate for heart motion, multiple information sources, such as image gradients, boundary detection, and motion prediction, are fused to achieve a robust tracking through the whole cardiac cycle. Furthermore, given the tracked LV endocardial boundaries, the disclosed methods correct for aliasing in the color Doppler data by using LV volume change between two neighboring frames.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

The invention claimed is:

1. A method of quantifying cardiac volume flow for an imaging sequence, the method comprising:
   receiving data representing three dimensions and color Doppler flow data over a plurality of frames;
   constructing a four-dimensional ventricular model based on the data representing three dimensions for the plurality of frames, the four-dimensional ventricular model comprising a sampling plane configured to measure the cardiac volume flow;
   computing volume flow samples based on the sampling plane and the color Doppler flow data; and
   correcting the volume flow samples for aliasing based on volumetric change in the four-dimensional ventricular model between successive frames of the plurality of frames.

2. The method of claim 1, wherein correcting the flow samples for aliasing comprises determining a de-aliasing correction factor based on a ratio between the volumetric change in the four-dimensional ventricular model and the computed volume flow samples for the successive frames.

3. The method of claim 1, wherein constructing the four-dimensional ventricular model comprises:
   tracking motion of a ventricular boundary between the successive frames; and
   adjusting the sampling plane based on the tracked motion.

4. The method of claim 3, wherein tracking the motion comprises:
   determining temporal displacement of model points between successive frames of the plurality of frames; and
   finding deformations, with a boundary detecting tracker, in each frame of the plurality of frames with maximal probability.

5. The method of claim 3, wherein tracking the motion comprises propagating anatomical boundaries and deformations using a Bayesian framework.

6. The method of claim 1, wherein constructing the four-dimensional ventricular model comprises optimizing the sampling plane for each frame of the plurality of frames.

7. The method of claim 1, wherein constructing the four-dimensional ventricular model comprises aligning temporal deformations in the four-dimensional ventricular model via four-dimensional generalized procrustes analysis.

8. The method of claim 1, wherein constructing the four-dimensional ventricular model comprises computing a low-dimensional embedding based on aligned training sequences.

9. The method of claim 1, wherein constructing the four-dimensional ventricular model comprises grouping motion sequences with hierarchical K-means clustering.

10. The method of claim 1, wherein the sampling plane is one of a plurality of sampling planes defined by the four-dimensional ventricular model.

11. The method of claim 1, wherein the data representing three dimensions is based on volume color Doppler data.

12. A system for quantifying cardiac volume flow for an imaging sequence, the system comprising:
   an image acquisition system configured to capture data representing three dimensions and color Doppler flow data over a plurality of frames; and
   a processor in communication with the image acquisition system to receive the data representing three dimensions and the color Doppler flow data and configured to:
   construct a four-dimensional ventricular model based on the data representing three dimensions, the four-dimensional ventricular model being configured to track motion of a ventricular boundary between successive frames of the plurality of frames;
   define a sampling plane based on the four-dimensional ventricular model for a first frame of the plurality of frames, the sampling plane being configured to measure the cardiac volume flow;
   adjust the sampling plane for a second frame of the plurality of frames based on the motion tracked by the four-dimensional ventricular model; and
   sample the color Doppler flow data for the second frame via the adjusted sampling plane.

13. The system of claim 12, wherein the processor is further configured to correct the sampled color Doppler flow data for aliasing based on volumetric change in the ventricular model between successive frames of the plurality of frames.

14. The system of claim 13, wherein the processor is further configured to determine a de-aliasing correction factor based on a ratio between the volumetric change in the four-dimensional ventricular model and the sampled color Doppler flow data for the successive frames.

15. The system of claim 12, wherein the processor, in constructing the four-dimensional ventricular model, is further configured to:
   determine temporal displacement of model points between successive frames of the plurality of frames; and identify deformations in each frame of the plurality of frames with maximal probability.

16. The system of claim 12, wherein the processor, in constructing the four-dimensional ventricular model, is further configured to propagate anatomical boundaries and deformations using a Bayesian framework.

17. The system of claim 12, wherein the processor is further configured to optimize the sampling plane for each frame of the plurality of frames.

18. The system of claim 12, wherein the processor, in constructing the four-dimensional ventricular model, is further configured to align temporal deformations in the four-dimensional ventricular model via four-dimensional generalized procrustes analysis.

19. The system of claim 12, wherein the processor, in constructing the four-dimensional ventricular model, is further configured to compute a low-dimensional embedding based on aligned training sequences.

20. The system of claim 12, wherein the processor, in constructing the four-dimensional ventricular model, is further configured to group motion sequences with hierarchical K-means clustering.

* * * * *